United States Patent
Asai (10) Patent No.: US 10,055,819 B2
(45) Date of Patent: Aug. 21, 2018

(54) RADIATION IMAGING APPARATUS, RADIATION IMAGING METHOD, AND RADIATION IMAGING SYSTEM

(71) Applicant: CANON KABUSHIKI KAISHA, Tokyo (JP)

(72) Inventor: Hiroki Asai, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 155 days.

(21) Appl. No.: 15/162,937

(22) Filed: May 24, 2016

(65) Prior Publication Data
US 2016/0358330 A1   Dec. 8, 2016

(30) Foreign Application Priority Data
Jun. 3, 2015   (JP) .................................. 2015-113310

(51) Int. Cl.
*G06K 9/00* (2006.01)
*G06T 5/00* (2006.01)
*A61B 6/00* (2006.01)

(52) U.S. Cl.
CPC ............... *G06T 5/002* (2013.01); *A61B 6/52* (2013.01); *G06T 2207/10112* (2013.01); *G06T 2207/10116* (2013.01); *G06T 2207/20008* (2013.01)

(58) Field of Classification Search
None
See application file for complete search history.

(56) References Cited

U.S. PATENT DOCUMENTS

| | | | |
|---|---|---|---|
| 2005/0078793 A1* | 4/2005 | Ikeda | A61B 6/00 378/98.8 |
| 2012/0230469 A1 | 9/2012 | Yamanaka | |
| 2016/0331340 A1* | 11/2016 | Mako | A61B 6/5258 |

FOREIGN PATENT DOCUMENTS

| | | |
|---|---|---|
| JP | 4557697 B2 | 10/2010 |
| JP | 2012-183241 A | 9/2012 |

OTHER PUBLICATIONS

Co-pending U.S. Appl. No. 15/165,199, filed May 26, 2016.

* cited by examiner

*Primary Examiner* — Atiba O Fitzpatrick
(74) *Attorney, Agent, or Firm* — Fitzpatrick, Cella, Harper & Scinto (57) ABSTRACT

The radiation imaging apparatus includes: a correction data acquiring unit configured to acquire, from image data captured in a predetermined imaging mode, offset correction data corresponding to the predetermined imaging mode; a switching unit configured to switch an acquisition mode for acquiring the image data, depending on the predetermined imaging mode; and an image processing unit configured to subtract the offset correction data from a radiation image of an object to perform an offset correction process.

14 Claims, 4 Drawing Sheets

| IMAGING MODE NO. | SIZE [cm] | BINNING | FRAME RATE [fps] | OUTPUT GAIN |
|---|---|---|---|---|
| 1 | 43×43 | 3×3 | 30 | 20 |
| 2 | 43×43 | 2×2 | 5 | 3 |
| 3 | 43×43 | 1×1 | 1 | 1 |
| 4 | 30×30 | 2×2 | 30 | 10 |
| 5 | 15×15 | 1×1 | 15 | 5 |
| ... | ... | ... | ... | ... |

FIG. 3A $\swarrow 300$

| IMAGING TECHNIQUE | ACQUISITION MODE | IMAGING MODE NO. |
|---|---|---|
| A | 0 | 1 |
| | | 4 |
| B | 1 | 5 |
| C | 1 | 2 |
| | | 3 |

FIG. 3B $\swarrow 330$

| IMAGING TECHNIQUE | IMAGED PART | OUTPUT GAIN | ACQUISITION MODE |
|---|---|---|---|
| ANGIOGRAPHY | HEART | 10 | 1 |
| | LEGS | 5 | 1 |
| | | 3 | 0 |
| | | 1 | 0 |
| | ... | | |
| TOMOSYNTHESIS | CHEST | 3 | 1 |
| | ... | | |
| ... | | | |
| | | | |

FIG. 4

RADIATION IMAGING APPARATUS, RADIATION IMAGING METHOD, AND RADIATION IMAGING SYSTEM

BACKGROUND OF THE INVENTION

Field of the Invention

The present invention relates to a radiation imaging apparatus, a radiation imaging method, and a radiation imaging system, which are used for capturing radiation images.

Description of the Related Art

As radiation imaging apparatus, which are configured to capture a radiation image of an object with the use of radiation (e.g., X ray) transmitted through the object, radiation imaging apparatus capable of displaying a radiation image in real time have been widespread. Further, flat-panel radiation imaging apparatus (FPD) have also been proposed.

The FPD includes minute radiation detectors aligned on a quartz glass substrate in matrix. The radiation detectors each includes a lamination of a scintillator configured to convert radiation into visible light and a solid-state photodetector in which an amorphous semiconductor is sandwiched by a transparent conductive film and a conductive film. Further, solid-state photodetectors using a photodetector, e.g., a CCD or a CMOS, have been known. Further, radiation detectors configured to directly detect radiation with solid-state photodetectors without using any scintillator have been known.

The FPD is configured to detect a dose of radiation applied during a given accumulation time as a charge amount. Thus, when a radiation image of an object is captured, if charges irrelevant to application of radiation are present in the radiation detectors, the charges are superimposed on the radiation image as noise, with the result that the image quality of the radiation image is degraded.

For example, as charges causing noise, there are given residual charges that remain, after a radiation image is captured in previous imaging, based on the characteristics of the solid-state photodetectors and the scintillators. Further, as charges causing noise, there is dark current caused by charges generated mainly due to temperatures of the solid-state photodetectors. Besides, fixed noise caused due to defects unique to the radiation detectors is a factor to degrade the image quality of radiation images.

When a radiation image of an object is captured, as accumulation time of charges in which radiation is applied elapses, residual charges and charges of dark current components are also accumulated in proportion to the accumulation time, to thereby degrade the image quality of the radiation image. Thus, an offset correction process is performed in capturing a radiation image of an object in order to remove offset components due to residual charges and dark current charges accumulated during imaging, fixed noise, and other factors.

In general, the offset correction process is performed as follows: image data acquired without radiation application (non-exposure image data) is used as offset correction data, and the offset correction data is subtracted from a radiation image. In this case, capturing of radiation images of an object and acquisition of non-exposure image data (offset correction data) of the object are alternately performed, and the offset correction data is subtracted from the radiation images, to thereby perform the offset correction process. Further, non-exposure image data acquired before capturing of a radiation image of an object is used as offset correction data, and the offset correction data is subtracted from the radiation image, to thereby perform the offset correction process.

When capturing of radiation images of an object and acquisition of non-exposure image data (offset correction data) of the object are alternately performed, while afterimages can be reduced, there is a problem in that frame rates are decreased.

When offset correction data is acquired before capturing of a radiation image of an object, while frame rates are increased to enable high-speed continuous image capturing, e.g., moving image capturing, there is a problem in that afterimages cannot sufficiently be reduced. Further, dark current charges are changed due to temperatures of the radiation detectors, imaging conditions, or deterioration of sensors with time. Thus, there is a problem in that the accuracy of the offset correction process may not be sufficient when offset correction data is acquired before capturing of a radiation image of an object.

In this case, noise components are amplified depending on setting parameters such as output gains and frame rates. Further, afterimages are liable to be generated depending on imaged parts. Radiation images of imaged parts including metal or contrast agents have edges, and hence afterimages thereof are liable to be generated. Besides, in a technique using a plurality of radiation images, e.g., tomosynthesis or long-length imaging, afterimages are liable to be generated and diagnosis is hindered by the afterimages.

Further, in an ordinary FPD, dark current charges are liable to be unstable immediately after radiation detectors start driving and immediately after radiation application. Further, it has been known that residual charges generated after radiation application greatly change immediately after radiation application is finished. Thus, in order to stably perform the offset correction process, it is necessary to secure a certain period of time from start of driving of the radiation detectors to radiation image capturing or from previous radiation image capturing to next radiation image capturing. Meanwhile, it is desired that radiation images be captured in a short period of time immediately after the driving start or immediately after previous radiation image capturing in order to improve the operability of the radiation imaging apparatus.

In each of Japanese Patent Application Laid-Open No. 2012-183241 and Japanese Patent No. 4557697, there is proposed a technology of determining the stability and a variation amount of offset correction data with respect to time, to thereby acquire offset correction data, in order to maintain the accuracy of an offset correction process.

However, a determination unit configured to determine the stability and a variation amount of offset correction data, and a calculation unit configured to calculate those elements are needed, and hence a memory capacity and a circuit scale may be increased depending on image sizes, determination criteria, and frame rates.

SUMMARY OF THE INVENTION

The present invention has been made in view of the above-mentioned problems, and provides a radiation imaging apparatus capable of performing an optimal offset correction process depending on imaging modes, without any increase in memory capacity and circuit scale.

According to one embodiment of the present invention, there is provided a radiation imaging apparatus, including: a correction data acquiring unit configured to acquire, from image data captured in a predetermined imaging mode, offset correction data corresponding to the predetermined imaging mode; and a switching unit configured to switch an acquisition mode for acquiring the image data, depending on the predetermined imaging mode.

Further features of the present invention will become apparent from the following description of exemplary embodiments with reference to the attached drawings.

DESCRIPTION OF THE EMBODIMENTS

Figure 1A:
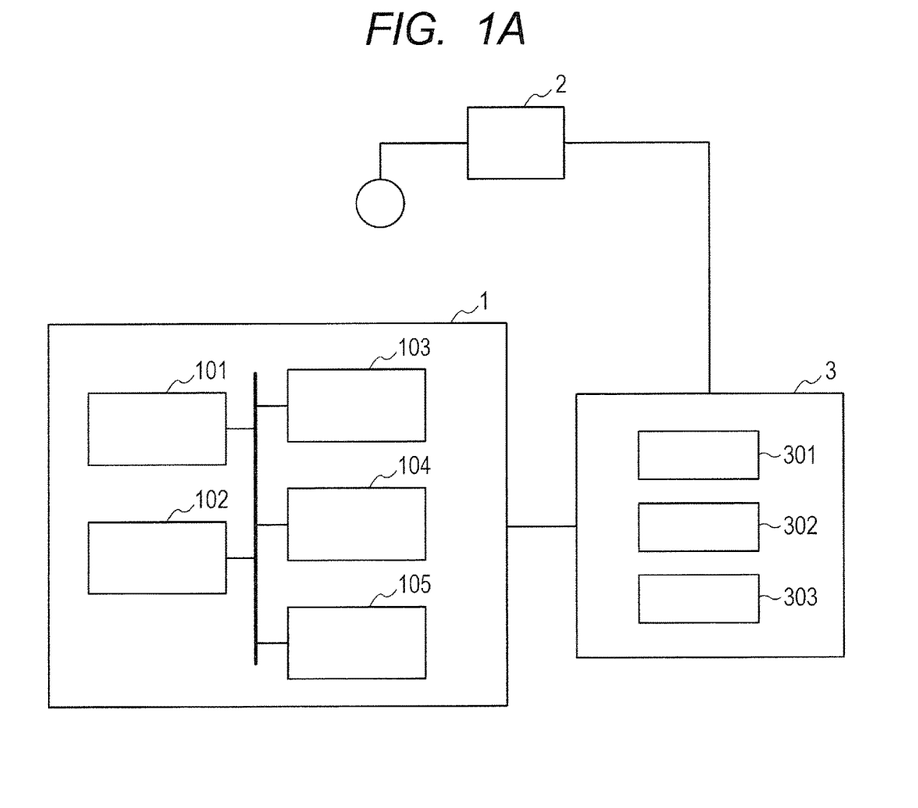
FIG. 1A is diagram for illustrating an example of a radiation imaging system according to an embodiment the present invention.

An example of an embodiment of the present invention is described in detail with reference to the drawings. FIG. 1A is a diagram for illustrating an example of a radiation imaging system according to this embodiment. As illustrated in FIG. 1A, the radiation imaging system includes a radiation imaging apparatus 1, a radiation generating apparatus 2 configured to apply radiation to the radiation imaging apparatus 1, and a control apparatus 3 configured to control the radiation imaging apparatus 1 and the radiation generating apparatus 2.

Figure 1B:
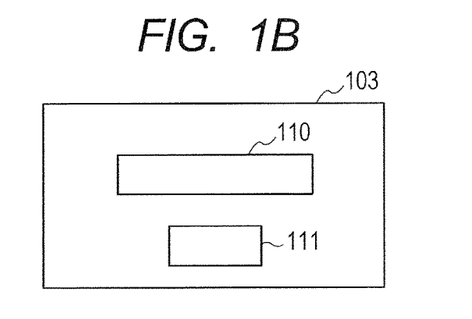
FIG. 1B is diagram for illustrating an example of a control unit in the radiation imaging system according to an embodiment the present invention.

The radiation imaging apparatus 1 includes a radiation detecting unit 101, an image processing unit 102, a control unit 103, a storage unit 104, and a communication unit 105. FIG. 1B is a diagram for illustrating the control unit 103. As illustrated in FIG. 1B, the control unit 103 includes a correction data acquiring unit 110 and a switching unit 111. The control apparatus 3 includes an input unit 301, a display unit 302, and a communication unit 303.

The radiation detecting unit 101 capable of detecting radiation includes a scintillator, a photodetector array, a driving circuit, and an A/D converter, and is configured to generate image data. The scintillator of the radiation detecting unit 101 has a base material of the scintillator which is excited with radiation having high energy passed through an object, and hence is configured to emit fluorescence in a visible region with recombination energy generated through recombination therein. This fluorescence is emitted by the base material itself, e.g., $CaWO_4$ or $CdWO_4$, or an emission center substance applied to the base material, e.g., CsI:Tl or ZnS:Ag.

The photodetector array is configured to output, through operation of the driving circuit, electric signals corresponding to an amount of fluorescence (a dose of radiation entering the scintillator) detected by each of pixels forming the photodetector array. The A/D converter is configured to convert signals output from the photodetector array into digital values, and output image data.

The image processing unit 102 is configured to subject image data output from the radiation detecting unit 101 to image processing such as a gain process and an offset correction process. The offset correction process is performed by subtracting, under control of the control unit 103, offset correction data (non-exposure image data) stored in the storage unit 104 from a radiation image. Further, the image processing unit 102 may be configured to perform other basic image processing, e.g., a gain correction process, in order to obtain radiation image data having low noise. In addition, the image processing unit 102 may be configured to perform image processing including image quality adjustment that is required by a user, e.g., gradation correction.

The control unit 103 is configured to perform processes relating to control of respective units of the radiation imaging apparatus 1, such as radiation image capturing and communication operation. For example, the control unit 103 is configured to give the driving circuit of the radiation detecting unit 101 instructions to acquire a radiation image, and give the storage unit 104 instructions to store the acquired radiation image.

The correction data acquiring unit 110 is configured to acquire, from image data (non-exposure image data) captured in a predetermined imaging mode, offset correction data corresponding to the imaging mode, and store the acquired offset correction data in the storage unit 104. The switching unit 111 is configured to switch an acquisition mode for acquiring image data (non-exposure image data), depending on the imaging mode. For example, the switching unit 111 is configured to output instructions to the driving circuit, to thereby switch the acquisition mode for acquiring image data (non-exposure image data) with the use of an acquisition mode switching table (switching table) stored in the storage unit 104.

Further, the control unit 103 is configured to transmit/receive data (image data, control signals, and other data) to/from the control apparatus 3 via the communication unit 105, and perform various processes based on the received data. For example, the control unit 103 is configured to read a program or other data stored in the storage unit 104, and control the radiation imaging apparatus 1 based on the program or other data. Further, the radiation imaging apparatus 1 may be controlled by a control signal generating circuit formed, for example, of an ASIC, or may be controlled by both of a program and a control circuit.

The storage unit 104 is configured to store information such as image data output from the radiation detecting unit 101 or the image processing unit 102, image data for the correction processes of the image processing unit 102 (offset correction data, gain correction data, and other data), imaging mode information, acquisition mode information (a switching table for switching the acquisition mode for acquiring offset correction data), and log information representing results of internal processing.

Further, when the control unit 103 is the one using software, e.g., a CPU, the storage unit 104 is configured to also store the software. The storage unit 104 can be implemented without any specific restriction, and the storage unit 104 may be implemented by one or a plurality of memory devices or HDDs, a volatile or non-volatile storage unit, or the combination thereof.

The communication unit 105 is implemented with the use of a wireless LAN, a wired LAN, or a communication module for public networks, and is configured to transfer various kinds of data (image data subjected to the image processing in the image processing unit 102, and log information) to the outside. For example, the communication unit 105 is configured to communicate to/from the control apparatus 3.

The control apparatus 3 is configured to display captured images, receive imaging orders, and input imaging information. The control apparatus 3 includes the input unit 301 with which a user can input various kinds of data, the display unit 302 configured to display radiation images, and the communication unit 303 configured to transmit/receive data to/from the radiation imaging apparatus 1.

The input unit 301 is used for receiving operation from the user. The input unit 301 can be implemented without any specific restriction as long as the input unit 301 can receive inputs from the user. For example, the input unit 301 is realized by various switches, a keyboard, and a touch panel that are operated by the user. The display unit 302 is configured to display radiation images received from the radiation imaging apparatus 1, and notify the user of states of the radiation imaging apparatus 1, for example. The display unit 302 is implemented without any specific restriction, and is realized by, for example, an LED, an LCD, and a monitor.

The communication unit 303 is used for communication between the communication unit 105 of the radiation imaging apparatus 1 and the control apparatus 3, and is configured to acquire image data output from the radiation imaging apparatus 1, and control data communication between the radiation imaging apparatus 1 and the control apparatus 3. The communication unit 303 is implemented without any specific restriction, and is realized with the use of a wireless LAN, a wired LAN, or a communication module for public networks.

Figure 2:
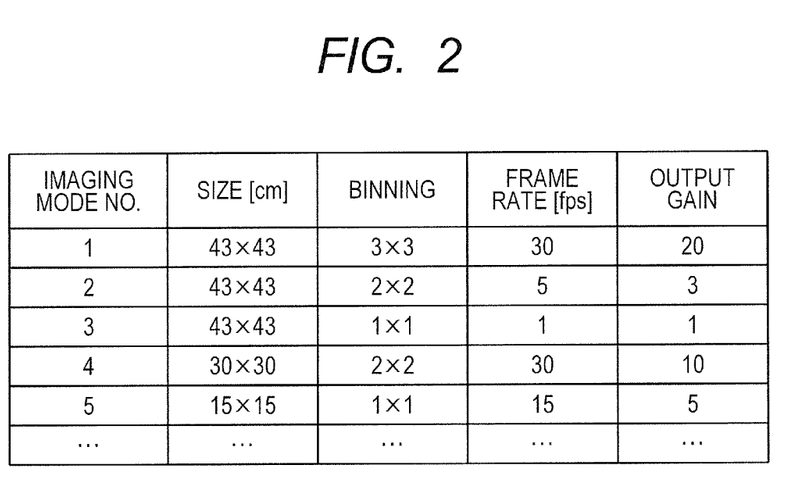
FIG. 2 is a table for showing examples of setting parameters of imaging modes.
Figure 3A:
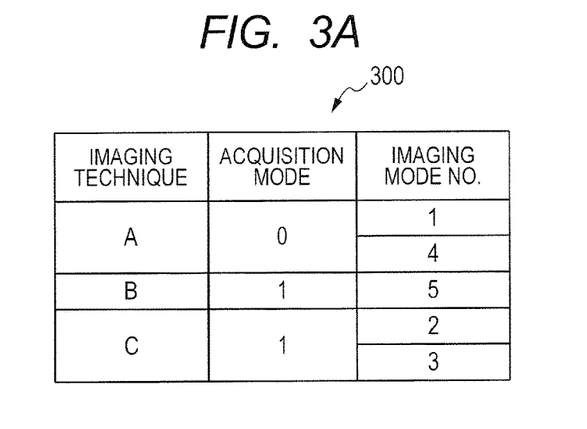
FIG. 3A is a diagram for showing an example of a switching table based on the imaging modes depending on imaging techniques.

Now, the imaging mode information and the acquisition mode are described. FIG. 2 is a table for showing examples of setting parameters of the imaging modes including the size, the binning, the frame rate, and the output gain of the image mode. The radiation imaging apparatus 1 has a plurality of imaging modes, and selectively uses an imaging mode suitable for an imaging technique. For example, as shown in FIG. 3A, an imaging technique A uses imaging modes No. 1 and No. 4, an imaging technique B uses an imaging mode No. 5, and an imaging technique C uses imaging modes No. 2 and No. 3. In this case, an acquisition mode associated with the imaging technique is stored in the storage unit 104 as a switching table 300.

The acquisition modes of FIG. 3A are modes for acquiring image data (non-exposure image data), and represented by "0" and "1". Here, the acquisition mode represented by "0" is an acquisition mode of acquiring image data (non-exposure image data) after imaging of an object. In this case, offset correction data is acquired after imaging of an object. Further, the acquisition mode represented by "0" is an acquisition mode of alternately performing imaging of an object and acquisition of offset correction data.

In this case, the correction data acquiring unit 110 acquires offset correction data at time intervals of continuous imaging of an object. For example, the correction data acquiring unit 110 acquires offset correction data (first offset correction data) at time intervals of continuous imaging of an object (for example, capturing of a first radiation image and capturing of a second radiation image). Further, the correction data acquiring unit 110 acquires offset correction data (second offset correction data) at the time intervals of continuous imaging of the object (for example, capturing of the second radiation image and capturing of a third radiation image).

The image processing unit 102 performs the offset correction process by alternately inputting radiation images of an object and offset correction data, and subtracting, from the radiation images of the object, the offset correction data acquired immediately after imaging of the object. For example, the image processing unit 102 subtracts the first offset correction data from the first radiation image, and subtracts the second offset correction data from the second radiation image, to thereby perform the offset correction process. In this manner, capturing of radiation images of an object and acquisition of non-exposure image data (offset correction data) of the object are alternately performed, and the offset correction data is subtracted from the radiation images, to thereby perform the offset correction process.

The acquisition mode represented by "1" is an acquisition mode of acquiring image data (non-exposure image data) before imaging of an object. In this case, offset correction data is acquired before imaging of an object. The image processing unit 102 subtracts, from a radiation image of an object, image data (non-exposure image data) acquired as offset correction data before imaging of the object, to thereby perform the offset correction process.

In this way, in the case of an imaging mode in which influences of afterimages on radiation images are strong and it is necessary to reduce the afterimages, the switching unit 111 switches the acquisition mode for acquiring image data to "0". For example, in an imaging mode in which tomosynthesis or slot-scan, which is a kind of techniques of long-length imaging, is performed, a plurality of radiation images of an object are recombined, and hence influences of afterimages are strong. In this case, "0" is registered as the acquisition mode in the switching table 300 so that suitable radiation images with reduced afterimages can be acquired, to thereby contribute to appropriate diagnosis with the radiation image.

The switching unit 111 may switch the acquisition mode based on imaged parts, or may switch the acquisition mode based on time elapsed since capturing of an image with radiation application (exposure image). Further, the switching unit 111 may switch the acquisition mode based on at least one of the size, the binning, the frame rate, or the output gain of the imaging mode. An acquisition mode corresponding to those switching conditions is stored in the storage unit 104 as a switching table.

For example, when setting values of output gains are large, artifacts are also large. Thus, the switching unit 111 sets a predetermined threshold (for example, an output gain of 10), and switches the acquisition mode to "0" in the imaging modes No. 1 and No. 4 having the output gains of the threshold or more. Further, the switching unit 111 switches the acquisition mode to "1" in the imaging modes No. 2, No. 3, and No. 5 having the output gains of less than the threshold.

In this case, in an imaging mode having an output gain of a threshold defined in advance or more, the image processing unit 102 subtracts, from a radiation image of the object, offset correction data acquired after imaging of an object, to thereby perform the offset correction process. Further, in an imaging mode having an output gain of less than the threshold defined in advance, the image processing unit 102 subtracts, from a radiation image of the object, offset correction data acquired before imaging of an object, to thereby perform the offset correction process.

Further, when frame rates are slow, accumulation time is long and influences of afterimages are strong. Thus, the switching unit 111 sets a predetermined threshold (for example, a frame rate of 10), and switches the acquisition mode to "1" in the imaging modes No. 1, No. 4, and No. 5 having the frame rates of the threshold or more. Further, the switching unit 111 switches the acquisition mode to "0" in the imaging modes No. 2 and No. 3 having the frame rates of less than the threshold.

In this case, in an imaging mode having a frame rate of a threshold defined in advance or more, the image processing unit 102 subtracts, from a radiation image of the object, offset correction data acquired before imaging of an object, to thereby perform the offset correction process. Further, in an imaging mode having a frame rate of less than the threshold defined in advance, the image processing unit 102 subtracts, from a radiation image of the object, offset correction data acquired after imaging of an object, to thereby perform the offset correction process.

Further, depending on imaged parts, radiation images have edges and afterimages are conspicuous. Thus, the switching unit 111 switches the acquisition mode to "0" in an imaging mode of imaging predetermined imaged parts (for example, parts in which metal is used for bones or joints, and parts in which barium or contrast agents are used for examination of gastrointestinal tract). Further, the switching unit 111 switches the acquisition mode to "1" in an imaging mode of imaging imaged parts other than the above.

Further, high frame rates are needed for imaged parts such as hearts. Thus, the switching unit 111 may put, between the imaged part and the frame rate (the setting parameters of the imaging mode), a high priority on the frame rate rather than the imaged part, and switch an acquisition mode enabling high-speed imaging operation to "1" based on the frame rate with the high priority.

In this manner, the switching unit 111 may put a priority on at least one of the imaging technique, the imaged part, the size, the binning, the frame rate, or the output gain of the imaging mode, and switch the acquisition mode based on the priority. For example, a priority may be put on at least one of the size, the binning, the frame rate, or the output gain of the imaging mode, and the switching unit 111 may switch the acquisition mode based on the priority. Further, a priority may be put on at least one of the imaging technique or the imaged part of the imaging mode, and the switching unit 111 may switch the acquisition mode based on the priority.

Further, an afterimage is liable to be generated on a radiation image of an object when time elapsed since previous capturing of an image with radiation application (exposure image) is short. Thus, the switching unit 111 may set a predetermined threshold, and switch the acquisition mode to "0" when time elapsed since capturing of an exposure image is the threshold or more. Further, the switching unit 111 may switch the acquisition mode to "1" when time elapsed since capturing of an exposure image is less than the threshold.

Figure 3B:
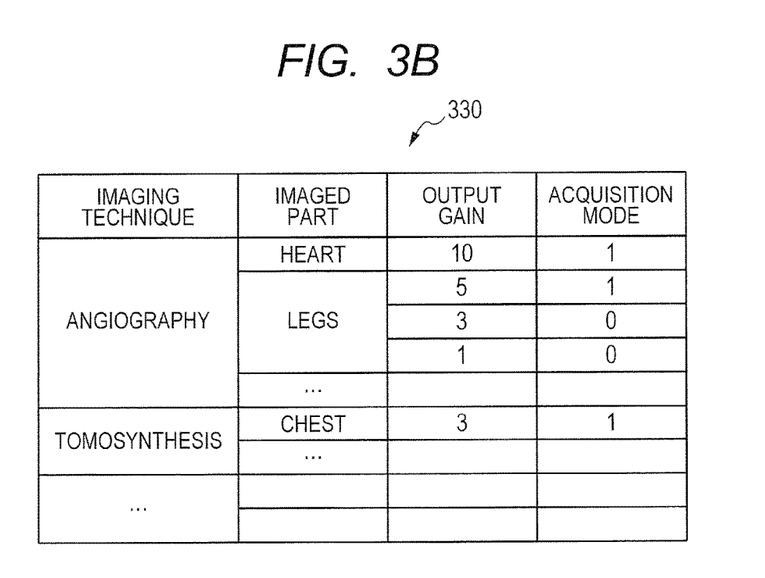
FIG. 3B is a diagram for showing an example of a hierarchized switching table.

Further, at least two of the imaging technique, the imaged part, the size, the binning, the frame rate, and the output gain of the imaging mode may be hierarchically classified, and the switching unit 111 may switch the acquisition mode based on the classification. For example, as shown in FIG. 3B, the imaging technique, the imaged part, and the output gain are hierarchized, and an acquisition mode based on the hierarchical classification is stored in the storage unit 104 as a switching table 330. The switching unit 111 may switch the acquisition mode based on the hierarchical classification.

Figure 4:
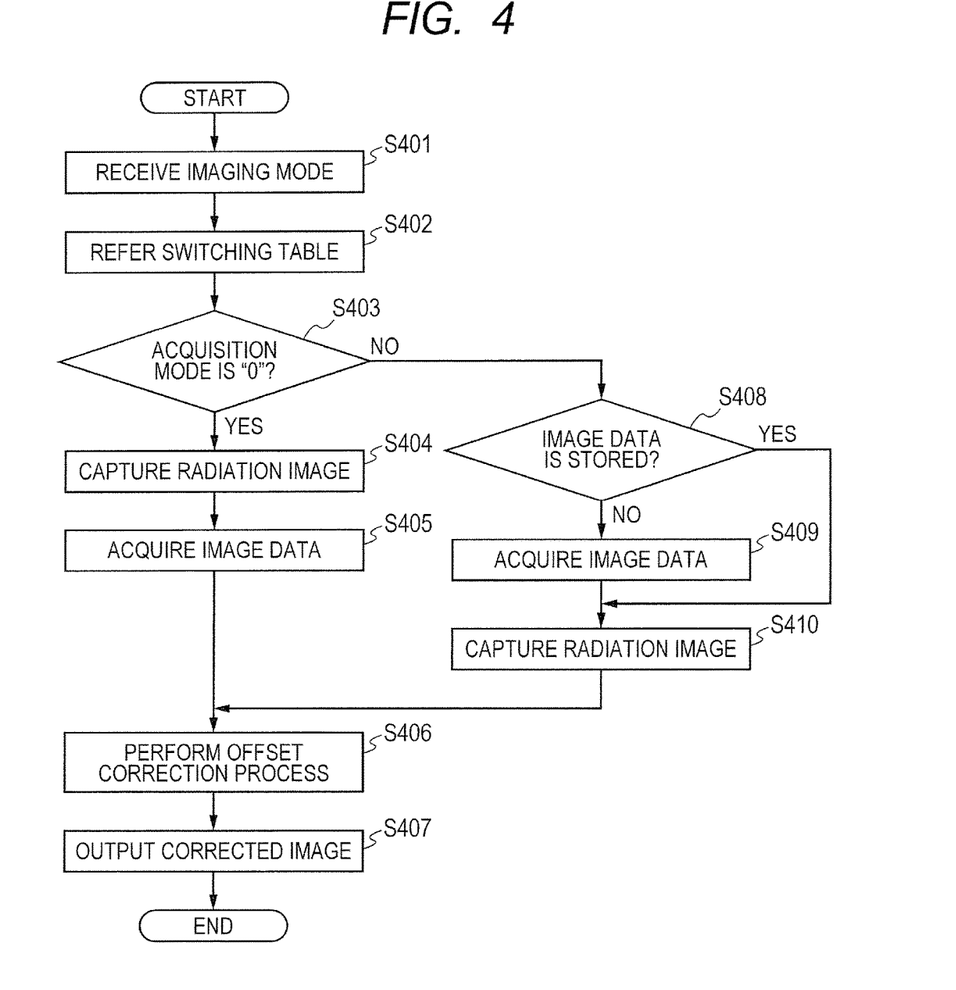
FIG. 4 is a flowchart for illustrating an example of operation of a radiation imaging apparatus according to the embodiment of the present invention.

Next, with reference to FIG. 4, the image processing including the offset correction process is described. FIG. 4 is a flowchart for illustrating an example of operation of the radiation imaging apparatus according to this embodiment.

In Step S401, a user inputs an imaging mode for capturing a radiation image of an object to the input unit 301 of the control apparatus 3, and the radiation imaging apparatus 1 receives the imaging mode via the communication units 105 and 303. In this case, the display unit 302 may display imaging modes so that the user can select an imaging mode.

In Step S402, the switching unit 111 refers to a switching table stored in the storage unit 104 depending on the imaging mode.

In Step S403, the acquisition mode for acquiring image data (non-exposure image data) is switched depending on the imaging mode. In this case, the display unit 302 may display acquisition modes so that the user can see the acquisition modes. In Step S403, when the acquisition mode is switched to "0", the processing proceeds to Step S404 and subsequent steps where image data (non-exposure image data) is acquired after imaging of the object, and imaging of the object and acquisition of offset correction data of the object are alternately performed.

In Step S404, the radiation generating apparatus 2 applies radiation to the radiation imaging apparatus 1, and the radiation imaging apparatus 1 captures a radiation image of the object in the predetermined imaging mode. In Step S405, the correction data acquiring unit 110 acquires, from the image data (non-exposure image data) captured in the predetermined imaging mode, offset correction data corresponding to the imaging mode in Step S404. In this case, the correction data acquiring unit 110 acquires, as offset correction data, non-exposure image data captured in the same imaging mode as one for the radiation image captured in Step S404.

In Step S406, the image processing unit 102 subtracts the offset correction data from the radiation image, to thereby perform the offset correction process. In Step S407, the image processing unit 102 outputs a corrected image subjected to the offset correction process in Step S406.

In Step S403, when the acquisition mode is switched to "1", the processing proceeds to Step S408 and subsequent steps where image data (non-exposure image data) is acquired before imaging of the object.

In Step S408, the correction data acquiring unit 110 determines whether or not image data (non-exposure image data) in the imaging mode to be used for imaging in Step S410 is stored in the storage unit 104. When the non-exposure image data is not stored, the processing proceeds to Step S409. When the non-exposure image data is stored, the correction data acquiring unit 110 acquires the non-exposure image data as offset correction data, and the processing proceeds to Step S410.

In Step S409, the correction data acquiring unit 110 acquires, from image data (non-exposure image data) captured in the predetermined imaging mode, offset correction data corresponding to the imaging mode in Step S410. In this case, the correction data acquiring unit 110 acquires, as offset correction data, non-exposure image data captured in the same imaging mode as one for a radiation image to be captured in Step S410.

The correction data acquiring unit 110 may acquire offset correction data from a plurality of pieces of non-exposure image data. For example, the correction data acquiring unit 110 may acquire, as offset correction data, an average of a plurality of pieces of non-exposure image data.

In Step S410, the radiation generating apparatus 2 applies radiation to the radiation imaging apparatus 1, and the radiation imaging apparatus 1 captures the radiation image of the object in the predetermined imaging mode. Then, the processing proceeds to Step S406 and Step S407.

As described above, according to this embodiment, switching is made between the acquisition modes set in advance, depending on the imaging mode, with the result that an optimal offset correction process can be performed to improve the image quality of a radiation image of an object, without any increase in memory capacity and circuit scale.

According to the present invention, an optimal offset correction process is performed depending on the imaging mode, thereby being capable of improving the image quality of a radiation image of an object, without any increase in memory capacity and circuit scale.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-113310, filed Jun. 3, 2015, which is hereby incorporated by reference herein in its entirety.

What is claimed is:

1. A radiation imaging apparatus comprising a processor coupled to a storage medium programmed to function as:
   a correction data acquiring unit configured to acquire, from image data captured in a predetermined imaging mode, offset correction data corresponding to the predetermined imaging mode;
   a switching unit configured to switch an acquisition mode for acquiring the offset correction data, depending on the predetermined imaging mode; and
   an image processing unit configured to subtract the offset correction data from a radiation image of an object to perform an offset correction process,
   wherein the acquisition mode includes a first mode where the offset correction data is acquired after imaging of an object and a second mode where the offset correction data is acquired before imaging of the object.

2. The radiation imaging apparatus according to claim 1, wherein the switching unit is configured to switch the acquisition mode based on at least one of an imaging technique of the predetermined imaging mode or an imaged part.

3. The radiation imaging apparatus according to claim 1, wherein the switching unit is configured to switch the acquisition mode based on at least one of a size, binning, a frame rate, or an output gain of the predetermined imaging mode.

4. The radiation imaging apparatus according to claim 1, wherein the switching unit is configured to switch the acquisition mode to at least one of an acquisition mode of acquiring the image data before imaging of the object, or an acquisition mode of acquiring the image data after imaging of the object.

5. The radiation imaging apparatus according to claim 4,
   wherein the switching unit is configured to switch the acquisition mode to the acquisition mode of acquiring the image data after imaging of the object, and
   wherein the correction data acquiring unit is configured to acquire the offset correction data at time intervals of continuous imaging of the object.

6. The radiation imaging apparatus according to claim 1, wherein the correction data acquiring unit is configured to acquire the offset correction data from a plurality of pieces of the image data.

7. The radiation imaging apparatus according to claim 1, wherein the image processing unit is configured to subtract, in an imaging mode having an output gain of a threshold defined in advance or more, from the radiation image of the object, the offset correction data acquired after imaging of the object.

8. The radiation imaging apparatus according to claim 1, wherein the image processing unit is configured to subtract, in an imaging mode having an output gain of less than a threshold defined in advance, from the radiation image of the object, the offset correction data acquired before imaging of the object.

9. The radiation imaging apparatus according to claim 1, wherein the image processing unit is configured to subtract, in an imaging mode having a frame rate of a threshold defined in advance or more, from the radiation image of the object, the offset correction data acquired before imaging of the object.

10. The radiation imaging apparatus according to claim 1, wherein the image processing unit is configured to subtract, in an imaging mode having a frame rate of less than a threshold defined in advance, from the radiation image of the object, the offset correction data acquired after imaging of the object.

11. The radiation imaging apparatus according to claim 1, wherein the switching unit is configured to put a priority on at least one of a size, binning, a frame rate, or an output gain of the predetermined imaging mode, and to switch the acquisition mode based on the priority.

12. The radiation imaging apparatus according to claim 1, wherein the switching unit is configured to put a priority on at least one of an imaging technique or an imaged part of the predetermined imaging mode, and to switch the acquisition mode based on the priority.

13. A radiation imaging method comprising:
   acquiring, from image data captured in a predetermined imaging mode, offset correction data corresponding to the predetermined imaging mode; and switching an acquisition mode for acquiring the offset correction data, depending on the predetermined imaging mode, wherein the acquisition mode includes a first mode where the offset correction data is acquired after imaging of an object and a second mode where the offset correction data is acquired before imaging of the object.

14. A radiation imaging system comprising:

a radiation imaging apparatus comprising a processor coupled to a storage medium programmed to function as:
- a correction data acquiring unit configured to acquire, from image data captured in a predetermined imaging mode, offset correction data corresponding to the predetermined imaging mode;
- a switching unit configured to switch an acquisition mode for acquiring the offset correction data, depending on the predetermined imaging mode; and
- an image processing unit configured to subtract the offset correction data from a radiation image of an object to perform an offset correction process,
- wherein the acquisition mode includes a first mode where the offset correction data is acquired after imaging of an object and a second mode where the offset correction data is acquired before imaging of the object;

a radiation generating apparatus configured to apply radiation to the radiation imaging apparatus;

an input unit configured to input the predetermined imaging mode; and a display unit configured to display the acquisition mode.

* * * * *